US010119715B2

(12) United States Patent
Hou et al.

(10) Patent No.: US 10,119,715 B2
(45) Date of Patent: Nov. 6, 2018

(54) METHOD AND DEVICE FOR TURNING ON AIR CONDITIONER (71) Applicant: Xiaomi Inc., Beijing (CN)

(72) Inventors: Enxing Hou, Beijing (CN); Yun Yang, Beijing (CN); Changbing Chen, Beijing (CN)

(73) Assignee: Xiaomi Inc., Beijing (CN)

( * ) Notice: Subject to any disclaimer, the term of this patent is extended or adjusted under 35 U.S.C. 154(b) by 274 days.

(21) Appl. No.: 15/091,729

(22) Filed: Apr. 6, 2016

(65) Prior Publication Data
US 2016/0334124 A1  Nov. 17, 2016

(30) Foreign Application Priority Data

May 11, 2015 (CN) .......................... 2015 1 0236279

(51) Int. Cl.
*F24F 11/00* (2018.01)
*A61B 5/00* (2006.01)
(Continued)

(52) U.S. Cl.
CPC .............. *F24F 11/006* (2013.01); *A61B 5/01* (2013.01); *A61B 5/02055* (2013.01);
(Continued)

(58) Field of Classification Search
CPC ... A61B 5/01; A61B 5/02055; A61B 5/02416; A61B 5/02438; A61B 5/0245;
(Continued)

(56) References Cited

U.S. PATENT DOCUMENTS 9,766,959 B2 * 9/2017 Faaborg .................. G06F 9/546
2006/0142968 A1 6/2006 Han et al.
(Continued)

FOREIGN PATENT DOCUMENTS

CN 1654892 A 8/2005
CN 101004283 A 7/2007
(Continued)

OTHER PUBLICATIONS

First Office Action issued by the State Intellectual Property Office of the People's Republic of China (SIPO) dated Mar. 3, 2017, in counterpart Chinese Application No. 201510236279.8.
(Continued)

*Primary Examiner* — Chun Cao
(74) *Attorney, Agent, or Firm* — Finnegan, Henderson, Farabow, Garrett & Dunner LLP (57) ABSTRACT The present disclosure provides a method for turning on an air conditioner and a device for turning on an air conditioner, belonging to the field of smart home. The method includes: acquiring a sensor parameter collected by a sensor in a wearable device; determining a physiological parameter based on the sensor parameter; determining a change in a sleep state of a user wearing the wearable device based on the physiological parameter; detecting whether the change in the sleep state is in conformity with a predetermined condition; and turning on the air conditioner when the change in the sleep state is detected to be in conformity with the predetermined condition.

9 Claims, 5 Drawing Sheets (51) Int. Cl.
  *A61B 5/0205* (2006.01)
  *A61B 5/11* (2006.01)
  *G05B 15/02* (2006.01)
  *A61B 5/01* (2006.01)
  *F24F 11/30* (2018.01)
  *F24F 11/62* (2018.01)
  *A61B 5/024* (2006.01)
  *A61B 5/0245* (2006.01)
  *F24F 120/10* (2018.01)
  *F24F 120/14* (2018.01)
  *F24F 11/66* (2018.01)

(52) U.S. Cl.
  CPC ............ *A61B 5/02438* (2013.01); *A61B 5/11* (2013.01); *A61B 5/4812* (2013.01); *F24F 11/30* (2018.01); *F24F 11/62* (2018.01); *G05B 15/02* (2013.01); *A61B 5/0245* (2013.01); *A61B 5/02416* (2013.01); *A61B 5/681* (2013.01); *F24F 11/66* (2018.01); *F24F 2120/10* (2018.01); *F24F 2120/14* (2018.01)

(58) Field of Classification Search
  CPC ......... A61B 5/11; A61B 5/4812; A61B 5/681; G05B 15/02; F24F 11/006; F24F 11/0034; F24F 11/30; F24F 11/62; F24F 11/66; F24F 2011/0036; F24F 2011/0065; F24F 2120/10; F24F 2120/14
  USPC ........................................................ 700/276
  See application file for complete search history.

(56) References Cited

U.S. PATENT DOCUMENTS

| | | | |
|---|---|---|---|
| 2008/0234785 A1 | 9/2008 | Nakayama et al. | |
| 2010/0240982 A1* | 9/2010 | Westbrook ............. | A61B 5/087 600/391 |
| 2014/0316305 A1 | 10/2014 | Venkatraman et al. | |
| 2015/0105917 A1 | 4/2015 | Sasaki et al. | |
| 2015/0320588 A1* | 11/2015 | Connor ................. | A61F 7/0097 607/107 |
| 2017/0031334 A1* | 2/2017 | Medelius ........... | G05D 23/1905 |

FOREIGN PATENT DOCUMENTS

| | | | |
|---|---|---|---|
| CN | 201259620 | Y | 6/2009 |
| CN | 201514001 | U | 6/2010 |
| CN | 101813356 | A | 8/2010 |
| CN | 102043385 | A | 5/2011 |
| CN | 102192568 | A | 9/2011 |
| CN | 103836759 | A | 6/2014 |
| CN | 104154633 | A | 11/2014 |
| CN | 104302048 | A | 1/2015 |
| CN | 104394614 | A | 3/2015 |
| CN | 104598130 | A | 5/2015 |
| CN | 104896656 | A | 9/2015 |
| EP | 2522923 | A2 | 11/2012 |
| JP | H 09170797 | A | 6/1997 |
| JP | H 9-303842 | | 11/1997 |
| JP | 2004092918 | A | 3/2004 |
| JP | 2011149567 | A | 8/2011 |
| JP | 2012237501 | A | 12/2012 |
| KR | 20080056540 | A | 6/2008 |
| KR | 20120051124 | A | 5/2012 |

OTHER PUBLICATIONS

First Search Report issued by the State Intellectual Property Office of the People's Republic of China (SIPO) dated Mar. 3, 2017, in counterpart Chinese Application No. 201510236279.8.

International Search Report issued by the State Intellectual Property Office for the P.R. China (SIPO) dated Feb. 17, 2016, in counterpart International Application No. PCT/CN2015/090600.

Written Opinion issued by the State Intellectual Property Office for the P.R. China (SIPO) dated Feb. 17, 2016, in counterpart International Application No. PCT/CN2015/090600.

European Search Report and Opinion issued by the European Patent Office dated Sep. 12, 2016, in counterpart European Application No. 16159837.0-1602.

Notification of Reasons for Refusal issued by the Japanese Patent Office dated May 30, 2017, in counterpart Japanese Application No. 2016-518455.

* cited by examiner

METHOD AND DEVICE FOR TURNING ON AIR CONDITIONER

CROSS-REFERENCE TO RELATED APPLICATIONS

This application is based on and claims priority to Chinese Patent Application No. 201510236279.8, filed on May 11, 2015, the entire content of which is incorporated herein by reference.

TECHNICAL FIELD

The present disclosure generally relates to the field of smart home, and more particularly, to a method and a device for turning on an air conditioner.

BACKGROUND

Along with the gradual improvement of people's living standards, an air conditioner has become an essential household appliance in daily life and has greatly improved people's living quality.

Due to the relatively large power consumption of an air condition, at households without a heater, the air conditioner is usually turned off at night and turned on for heating before a user gets up during autumn and winter. In order to enable the room temperature to be heated to an appropriate temperature before the user wakes up, a conventional air conditioner is provided with a timing switching function, so that the user may set up a certain time point at which the air conditioner will be turned on. For example, if the user expects to get up at 7 o'clock, the air conditioner may be set up to be turned on for heating at 6:40.

SUMMARY

According to a first aspect of the present disclosure, there is provided a method for turning on an air conditioner. The method includes: acquiring a sensor parameter collected by a sensor in a wearable device; determining a physiological parameter based on the sensor parameter; determining a change in a sleep state of a user wearing the wearable device based on the physiological parameter; detecting whether the change in the sleep state is in conformity with a predetermined condition; and turning on the air conditioner when the change in the sleep state is detected to be in conformity with the predetermined condition.

According to a second aspect of the present disclosure, there is provided a device for turning on an air conditioner. The device includes a processor and a memory configured to store instructions executable by the processor. The processor is configured to: acquire a sensor parameter collected by a wearable device; determine a physiological parameter based on the sensor parameter; determine a change in a sleep state of a user wearing the wearable device based on the physiological parameter; detect whether the change in the sleep state is in conformity with a predetermined condition; and turn on the air conditioner when the change in the sleep state is detected to be in conformity with the predetermined condition.

According to a third aspect of the present disclosure, there is provided a non-transitory computer-readable storage medium having stored therein instructions that, when executed by a processor of a device, cause the device to perform a method for turning on an air conditioner. The method includes: acquiring a sensor parameter collected by a sensor in a wearable device; determining a physiological parameter based on the sensor parameter; determining a change in a sleep state of a user wearing the wearable device based on the physiological parameter; detecting whether the change in the sleep state is in conformity with a predetermined condition; and turning on the air conditioner when the change in the sleep state is detected to be in conformity with the predetermined condition.

The technical solution provided in embodiments of the present disclosure may have the following advantageous effect. The change in the sleep state of a user wearing the wearable device is determined on a basis of the physiological parameter, which is determined based on the sensor parameter collected by the wearable device. In the case that the change in the sleep state is in conformity with the predetermined condition, the air conditioner is turned on when the user wakes up, thereby ensuring that the room temperature has been adjusted to an appropriate temperature when the user wakes up. Besides, it is not required for the user to set up the time point at which the air conditioner will be turned on manually, thereby simplifying operations for users, and thus improving user experience.

It is to be understood that both the foregoing general description and the following detailed description are merely exemplary and explanatory, and not intended to limit the present disclosure.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of apparatuses and methods consistent with aspects related to the invention as recited in the appended claims.

Figure 1:
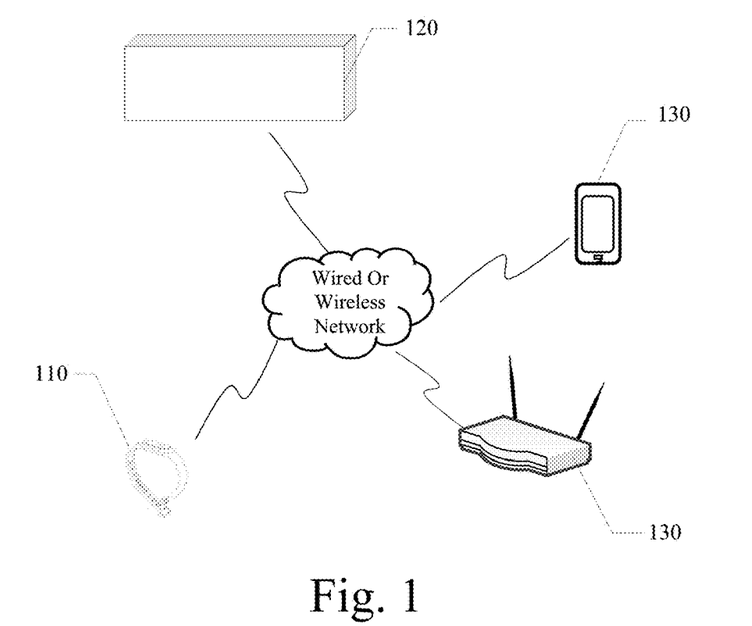
FIG. 1 is a schematic diagram showing an environment in which a method for turning on an air conditioner according to exemplary embodiments of the present disclosure may be implemented.

FIG. 1 is a schematic diagram showing an environment in which a method for turning on an air conditioner according to exemplary embodiments of the present disclosure may be implemented. Such environment includes a wearable device 110, an air conditioner 120, and at least one relay device 130.

The wearable device 110 may be a wearable smart device like a smart watch, a smart bracelet, or the like. The wearable device 110 includes a sensor, such as an infrared sensor, a piezoelectric sensor, a temperature sensor, a body movement sensor, and the like.

The relay device 130 may be a smart device, for example, a smart phone, a smart router, or the like.

The wearable device 110, the air conditioner 120, and the relay device 130 are connected by a wired or wireless network. A connection of short-distance wireless communication may be established directly between the wearable device 110 and the air conditioner 120 or between the wearable device 110 and a remote controller of the air conditioner 120. Alternatively, a connection of short-distance wireless communication may be also established indirectly between the wearable device 110 and the air conditioner 120 or between the wearable device 110 and a remote controller of the air conditioner 120 via the relay device 130.

Figure 2:
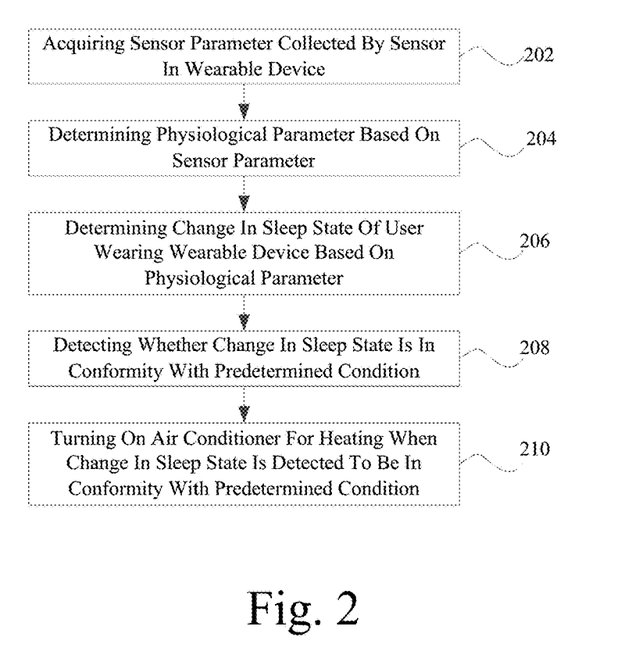
FIG. 2 is a flow chart showing a method for turning on an air conditioner, according to an exemplary embodiment of the present disclosure.

FIG. 2 is a flow chart showing a method for turning on an air conditioner, according to an exemplary embodiment of the present disclosure. Such method for turning on the air conditioner is used in the wearable device 110, the air conditioner 120, or the relay device 130 as shown in FIG. 1. As shown in FIG. 2, the method for turning on the air conditioner may include the following steps.

In step 202, a sensor parameter collected by a sensor in a wearable device is acquired.

In step 204, a physiological parameter is determined based on the sensor parameter.

In step 206, a change in a sleep state of a user corresponding to (e.g., wearing) the wearable device is determined based on the physiological parameter.

In step 208, it is detected whether the change in the sleep state is in conformity with a predetermined condition.

In step 210, the air conditioner is turned on for heating when the change in the sleep state is detected to be in conformity with the predetermined condition.

The physiological parameter includes at least one of a heart rate parameter, a body temperature parameter, and a body movement parameter. The determining of the physiological parameter based on the sensor parameter includes at least one of: determining the heart rate parameter based on a parameter collected by an infrared sensor or a piezoelectric sensor in the wearable device; determining the body temperature parameter based on a parameter collected by a temperature sensor in the wearable device; and determining the body movement parameter based on a parameter collected by a body movement sensor in the wearable device.

The sleep state includes at least a deep sleep state and a light sleep state. The predetermined condition includes a transition from the deep sleep state to the light sleep state.

Prior to turning on the air conditioner for heating, the method further may include determining an estimated length of time period $t_1$ during which the user will be in the light sleep state. The turning on the air conditioner for heating includes: turning on the air conditioner for heating immediately when the change in the sleep state is detected to be in conformity with the predetermined condition in the case of $t_1 \le t_2$; and turning on the air conditioner for heating after a time period ($t_1$-$t_2$) from the change in the sleep state being detected to be in conformity with the predetermined condition in the case of $t_1 > t_2$, in which $t_2$ represents an estimated length of time period during which a room temperature will be heated to a target temperature by the air conditioner.

The determining of the estimated length of time period $t_1$ during which the user will be in the light sleep state includes: acquiring historical sleep state information including a length of every historical time period during which the user was in the light sleep state; and determining an average length of the historical time periods during which the user was in the light sleep state as the estimated length of time period $t_1$.

Prior to turning on the air conditioner for heating, the method may further include: determining whether a time point of detecting, at which the change in the sleep state is detected to be in conformity with the predetermined condition, is within a predetermined time period; and turning on the air conditioner for heating when the time point of detecting is within the predetermined time period.

In summary, the method for turning on the air conditioner according to the embodiments of the present disclosure may determine the change in the sleep state of a user wearing the wearable device on a basis of the physiological parameter, which is determined based on the sensor parameter collected by the wearable device. In the case that the change in the sleep state is in conformity with the predetermined condition, the air conditioner is turned on for heating when the user wakes up, thereby ensuring that the room temperature has been elevated to an appropriate temperature when the user wakes up. Besides, the user is not required to manually set up the time of turning on the air conditioner. As a result, operations by the users may be simplified, and the user's experience may be improved.

Figure 3:
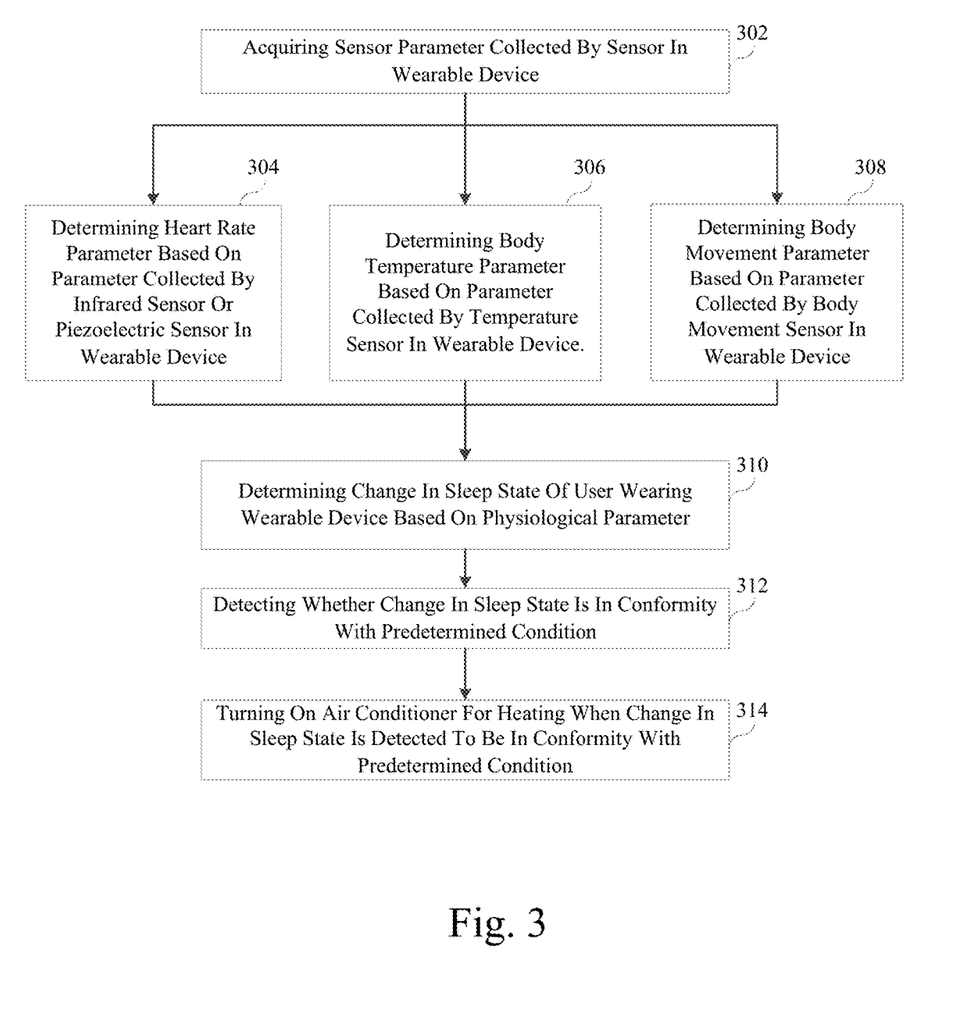
FIG. 3 is a flow chart showing a method for turning on an air conditioner, according to another exemplary embodiment of the present disclosure.

FIG. 3 is a flow chart showing a method for turning on an air conditioner, according to another exemplary embodiment of the present disclosure. Such method for turning on the air conditioner is used in the wearable device 110, the air conditioner 120, or the relay device 130 shown in FIG. 1. As shown in FIG. 3, the method for turning on the air conditioner may include the following steps.

In step 302, a sensor parameter collected by a sensor in a wearable device is acquired.

The wearable device may be provided with various kinds of sensors, such as an infrared sensor, a piezoelectric sensor, a temperature sensor, a body movement sensor, and the like.

In some embodiments of the present disclosure, at least one of the following physiological parameters may be determined based on the sensor parameter: a heart rate parameter, a body temperature parameter, and a body movement parameter. The method for determining various physiological parameters may be shown as follows.

In step 304, the heart rate parameter is determined based on a parameter collected by an infrared sensor or a piezoelectric sensor in the wearable device.

For example, the infrared sensor in the wearable device may emit an infrared ray generated by an infrared light emitting diode to a blood vessel in the body of a user wearing the wearable device, and collect an infrared signal transmitted or reflected from the blood passing through the blood vessel. A real-time heart rate in the user's body may be obtained after preamplifying, smoothing, and preforming related calculations on the infrared signal collected by the infrared sensor.

Alternatively, when the wearable device is provided with the piezoelectric sensor, the real-time heart rate the user may also be obtained by processing a change of the user's blood pressure.

In step 306, the body temperature parameter is determined based on a parameter collected by a temperature sensor in the wearable device.

When the wearable device is provided with the temperature sensor, it may collect a real-time temperature of body by the temperature sensor.

In step 308, the body movement parameter is determined based on a parameter collected by a body movement sensor in the wearable device.

When the wearable device is provided with the body movement sensor, it may collect a tiny movement by the body movement sensor, for example turning over, moving a limb, and the like.

In step 310, a change in a sleep state of the user corresponding to (e.g., wearing) the wearable device is determined based on the physiological parameter.

The user's sleep state may include a deep sleep state, a light sleep state, and a waking state. The physiological parameter of the user changes when the user's sleep state changes from one state to another. For example, when the sleep state of the user changes from the deep sleep state to the light sleep state, the user's heart rate, body temperature, and body movement may increase. Conversely, when the sleep state of the user changes from the light sleep state to the deep sleep state, the user's heart rate, body temperature, and body movement may decrease. The change in the user's sleep state may be determined by analyzing the changes of these physiological parameters. Specific algorithm for determining the user's sleep state by analyzing the physiological parameters may be established in accordance with actual conditions, which is not limited in the present disclosure.

In step 312, it is detected whether the change in the sleep state is in conformity with a predetermined condition.

In some embodiments of the present disclosure, the predetermined condition may be set as that the user's sleep state changes from the deep sleep state into the light sleep state.

Moreover, those skilled in the art may also set other predetermined conditions in accordance with user's usage condition, which is not limited in embodiments of the present disclosure. For example, the predetermined condition may be set as that the user's sleep state changes from the light sleep state into the waking state.

In step 314, the air conditioner is turned on for heating when the change in the sleep state is detected to be in conformity with the predetermined condition.

It may be determined that the user is about to wake up and ready to get up when the user's sleep state is detected as transiting into the light sleep state from the deep sleep state. At this time, the air conditioner may be turned on for heating, so that the room temperature will have been elevated to an appropriate temperature by the time the user gets up.

In embodiments of the present disclosure, all of the above-mentioned steps may be accomplished by the wearable device. For example, in the case that the wearable device is a smart bracelet, a sensor in the smart bracelet may collect the sensor parameter, and then the smart bracelet may determine the physiological parameter based on the sensor parameter, and send an instruction for turning on the air conditioner for heating to the air conditioner when the smart bracelet determines that the user is about to wake up based on the physiology parameter.

Alternatively, the above-mentioned steps may be accomplished by the air conditioner or the relay device. For example, the air conditioner acquires, from the smart bracelet, the sensor parameter collected by the sensor of the smart bracelet, determines the physiological parameter based on the sensor parameter, and turns on itself for heating when determining that the user is about to wake up based on the physiology parameter. As another example, a smart phone or a router acquires, from the smart bracelet, the sensor parameter collected by the sensor of the smart bracelet, determines the physiological parameter based on the sensor parameter, and sends an instruction to the air conditioner so as to turn on the air conditioner for heating when determining that the user is about to wake up based on the physiology parameter.

In summary, the method for turning on the air conditioner according to the embodiments of the present disclosure may determine the change in the sleep state of a user wearing the wearable device on a basis of the physiological parameter, which is determined based on the sensor parameter collected by the wearable device. In the case that the change in the sleep state is in conformity with the predetermined condition, the air conditioner is turned on for heating when the user wakes up, thereby ensuring that the room temperature has been elevated to an appropriate temperature when the user wakes up. Besides, the user is not required to manually set up the time of turning on the air conditioner. As a result, operations by the users may be simplified, and the users' experience may be improved.

Figure 4:
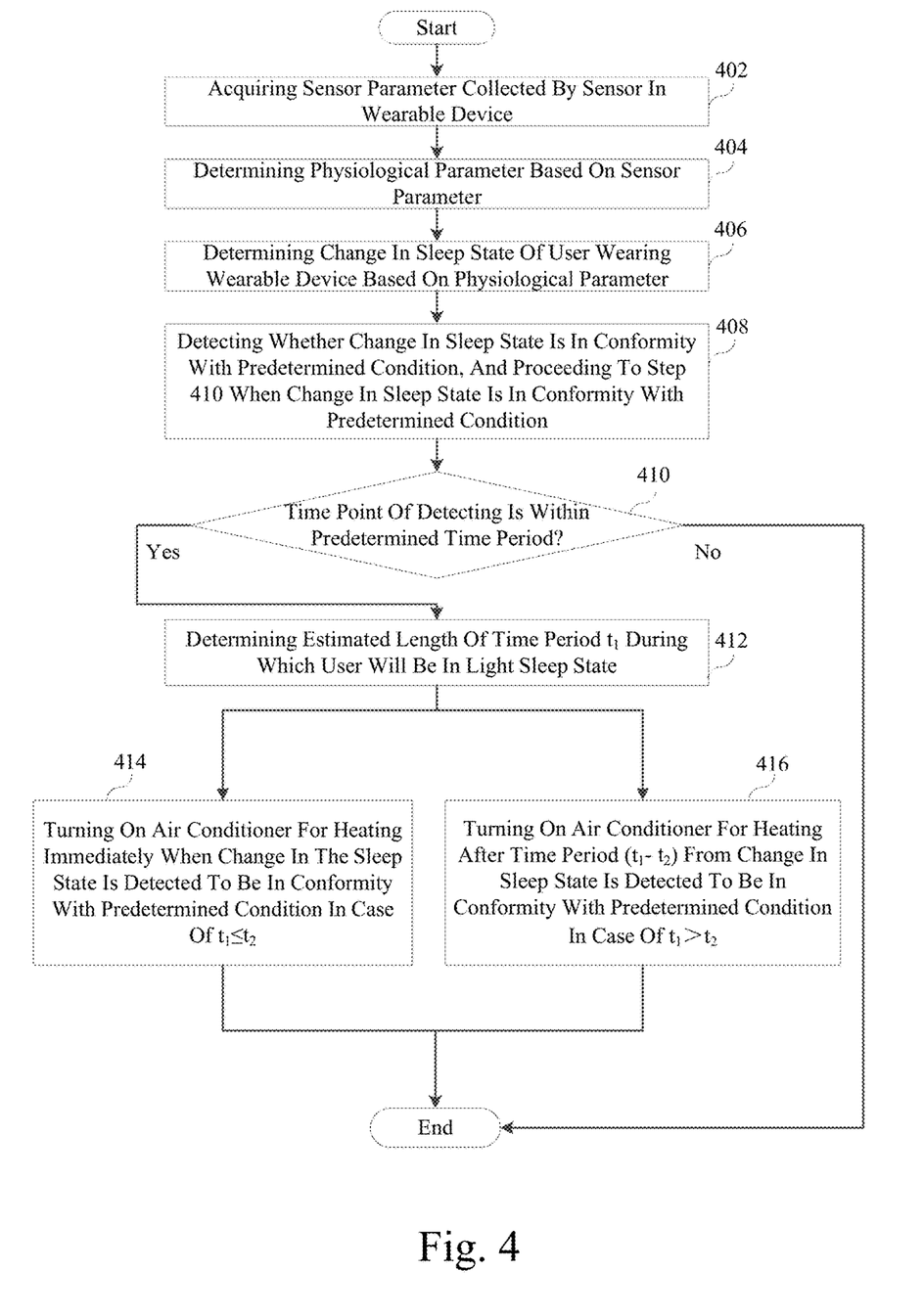
FIG. 4 is a flow chart showing a method for turning on an air conditioner, according to a further exemplary embodiment of the present disclosure.

FIG. 4 is a flow chart showing a method for turning on an air conditioner according to a further exemplary embodiment of the present disclosure. Such method for turning on the air conditioner is used in the wearable device 110, the air conditioner 120, or the relay device 130 as shown in FIG. 1. As shown in FIG. 4, the method for turning on the air conditioner may include the following steps.

In step 402, a sensor parameter collected by a sensor in a wearable device is acquired.

The wearable device may be provided with various kinds of sensors, such as an infrared sensor, a piezoelectric sensor, a temperature sensor, a body movement sensor, and the like.

In step 404, a physiological parameter is determined based on the sensor parameter.

In some embodiments of the present disclosure, the physiological parameter to be determined may include at least one of a heart rate parameter, a body temperature parameter, and a body movement parameter. The method for determining various physiological parameters may be similar as steps 304 to 308 in the embodiment shown in FIG. 3, the description of which is not repeated herein.

In step 406, a change in a sleep state of a user wearing the wearable device is determined based on the physiological parameter.

The user's sleep state may include a deep sleep state, a light sleep state, and a waking state. The physiological parameter of the user changes when the user's sleep state changes from one state to another. For example, when the sleep state of the user changes from the deep sleep state to the light sleep state, the user's heart rate, body temperature, and body movement may increase. Conversely, when the sleep state of the user changes from the light sleep state to the deep sleep state, the user's heart rate, body temperature, and body movement may decrease. The change in the user's sleep state may be determined by analyzing the changes of these physiological parameters.

In step 408, it is detected whether the change in the sleep state is in conformity with a predetermined condition. Step 410 is executed when the change in the sleep state is in conformity with the predetermined condition.

In some embodiments of the present disclosure, the predetermined condition may be set as that the user's sleep state changes from the deep sleep state to the light sleep state.

Moreover, those skilled in the art may also set other predetermined conditions in accordance with user's usage condition, which is not limited in embodiments of the present disclosure. For example, the predetermined condition may be set as that the user's sleep state changes from the light sleep state to the waking state.

In step 410, it is determined whether a time point of detecting is within a predetermined time period. Step 412 is executed if the time point of detecting is within the predetermined time period, otherwise the process ends.

The time point of detecting is a time point at which the change in the sleep state is detected to be in conformity with the predetermined condition.

In some cases, the user's sleep state changing from the deep sleep state to the light sleep state does not necessarily mean that the user is about to wake up and get up. For example, the user may suffer from insomnia in the midnight. In order to prevent the air conditioner from being turned on in this case, it may be further determined whether a time point of detecting, at which the change in the sleep state is detected to be in conformity with the predetermined condition, is within the predetermined time period. For example, it may be determined whether the time point of detecting is within a time period from 7 o'clock to 9 o'clock. If the time point of detecting is within the time period from 7 o'clock to 9 o'clock, then the subsequent steps are executed, otherwise the subsequent steps are not executed.

In step 412, historical sleep state information including a length of every historical time period during which the user was in the light sleep state is acquired, and an average length of the historical time periods during which the user was in the light sleep state is determined as an estimated length of time period $t_1$ during which the user will be in the light sleep state.

The time period between the light sleep state and the waking state varies across different users. If a user requires a longer time period for transitioning from the light state to the waking state, then turning on the air conditioner in advance may result in a waste of electric power. In order to improve the heating effect and save the electric energy, the historical sleep state information including a length of every historical time period during which the user was in the deep sleep state, the light sleep state, and the waking state may be acquired, respectively; and an average length of the historical time periods during which the user was in the light sleep state may be determined as the estimated length of time period $t_1$.

The historical sleep state information may be automatically recorded by the wearable device or other devices such as a smart phone, so as to be checked by the user or called by other third-party applications.

In step 414, the air conditioner is turned on for heating immediately when the change in the sleep state is detected to be in conformity with the predetermined condition in the case of $t_1 \leq t_2$, in which $t_2$ represents an estimated length of time period during which a room temperature will be heated to a target temperature by the air conditioner.

In the case that the estimated length of time period $t_1$ during which the user will in the light sleep state is shorter than the estimated length of time period $t_2$ during which the room temperature will be heated to the target temperature by the air conditioner, which indicates that the room temperature will not be heated to an appropriate temperature at the time the user wakes up, then the air conditioner needs to be turned on for heating immediately. The estimated length of time period $t_2$ during which the room temperature will be heated to the target temperature may be determined by calculating in accordance with the air conditioner's power and heating efficiency, and a temperature difference between the current room temperature and the target temperature.

In step 416, the air conditioner is turned on for heating after a time period $(t_1-t_2)$ from the change in the sleep state being detected to be in conformity with the predetermined condition in the case of $t_1 > t_2$.

In the case that the estimated length of time period $t_1$ during which the user will in the light sleep state is longer than the estimated length time period $t_2$ during which the room temperature will be heated to the target temperature by the air conditioner, which indicates that the room temperature will be heated to an appropriate temperature before the user wakes up, then the air conditioner needs to be turned on for heating after the time period $(t_1-t_2)$, other than immediately, so that the room temperature can be heated to the appropriate temperature right at the time when the user wakes up, thereby avoiding unnecessary waste of electric power.

In embodiments of the present disclosure, all of the above-mentioned steps may be accomplished by the wearable device. For example, in the case that the wearable device is a smart bracelet, a sensor in the smart bracelet may collect the sensor, and then the smart bracelet may determine the physiological parameter based on the sensor parameter, and send an instruction for turning on the air conditioner for heating to the air conditioner when the smart bracelet determines that the user is about to wake up based on the physiology parameter.

Alternatively, the above-mentioned steps may be accomplished by the air conditioner or the relay device. For example, the air conditioner acquires, from the smart bracelet, the sensor parameter collected by the sensor of the smart bracelet, determines the physiological parameter based on the sensor parameter, and turns on itself for heating when determining that the user is about to wake up based on the physiology parameter. As another example, a smart phone or a router acquires, from the smart bracelet, the sensor parameter collected by the sensor of the smart bracelet, determines the physiological parameter based on the sensor parameter, and sends an instruction to the air conditioner so as to turn on the air conditioner for heating when determining that the user is about to wake up based on the physiology parameter.

In summary, the method for turning on the air conditioner according to the embodiments of the present disclosure may determine the change in the sleep state of a user wearing the wearable device on a basis of the physiological parameter, which is determined based on the sensor parameter collected by the wearable device. In the case that the change in the sleep state is in conformity with the predetermined condition, the air conditioner is turned on for heating when the user wakes up, thereby ensuring that the room temperature has been elevated to an appropriate temperature when the user wakes up. Besides, the user is not required to manually set up the time of turning on the air conditioner. As a result, operations by the users may be simplified, and the users' experience may be improved.

Besides, the method for turning on the air conditioner according to the embodiments of the present disclosure may determine the estimated length of time period during which the user will be in the light sleep state based on the user's historical sleep state information, and determine the specific time of turning on the air conditioner based on the relationship between the estimated length of time period during which the user will be in the light sleep state and the estimated length of time period during which the room temperature will be heated to the target temperature, thereby avoiding unnecessary electric power consumption.

In addition, the method for turning on the air conditioner according to the embodiments of the present disclosure may turn on the air conditioner for heating only if the time point of detecting, at which the change in the sleep state is detected to be in conformity with the predetermined condition, is within the predetermined time period, thereby preventing the air conditioner from being turned on when it should not be turned on.

The following device embodiments of the present disclosure may be used to perform the method embodiments of the present disclosure. For details not disclosed in the device embodiments of the present disclosure, reference is made to the method embodiments of the present disclosure.

Figure 5:
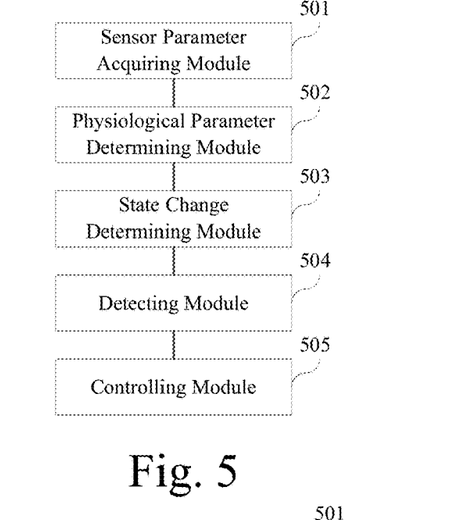
FIG. 5 is a block diagram showing a device for turning on an air conditioner, according to an exemplary embodiment of the present disclosure.

FIG. 5 is a block diagram showing a device for turning on an air conditioner, according to an exemplary embodiment of the present disclosure. Such device for turning on the air conditioner may be used in the wearable device 110, the air conditioner 120, or the relay device 130 as shown in FIG. 1, so as to execute all or part of the steps of the method shown in any one of FIGS. 2 to 4. As shown in FIG. 5, such device for turning on the air conditioner includes, but is not limited to, a sensor parameter acquiring module 501, a physiological parameter determining module 502, a state change determining module 503, a detecting module 504, and a controlling module 505.

The sensor parameter acquiring module 501 is configured to acquire a sensor parameter collected by a sensor in a wearable device.

The physiological parameter determining module 502 is configured to determine a physiological parameter based on the sensor parameter.

The state change determining module 503 is configured to determine a change in a sleep state of a user wearing the wearable device based on the physiological parameter.

The detecting module 504 is configured to detect whether the change in the sleep state is in conformity with a predetermined condition.

The controlling module 505 is configured to turn on the air conditioner for heating when the detecting module 504 detects that the change in the sleep state is in conformity with the predetermined condition.

In summary, the device for turning on the air conditioner according to the embodiments of the present disclosure may determine the change in the sleep state of a user wearing the wearable device on a basis of the physiological parameter, which is determined based on the sensor parameter collected by the wearable device. In the case that the change in the sleep state is in conformity with the predetermined condition, then the air conditioner is turned on for heating when the user wakes up, thereby ensuring that the room temperature has been elevated to an appropriate temperature when the user wakes up. Besides, the user is not required to manually set up the time of turning on the air conditioner. As a result, operations by the users may be simplified, and the users' experience may be improved.

Figure 6:
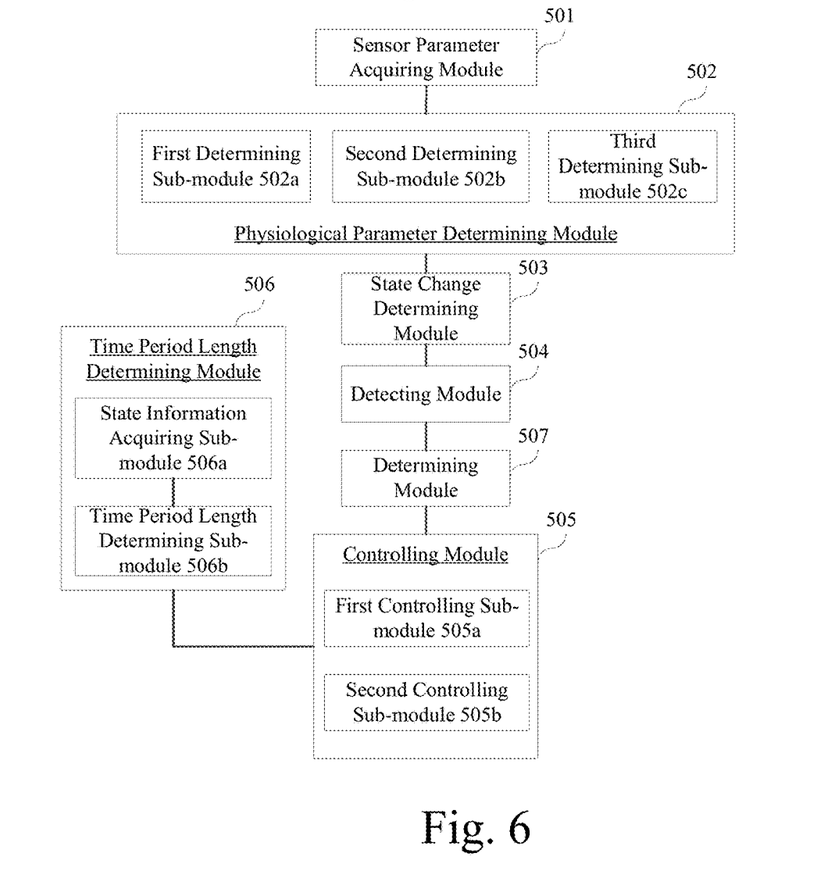
FIG. 6 is a block diagram showing a device for turning on an air conditioner, according to another exemplary embodiment of the present disclosure.

FIG. 6 is a block diagram showing a device for turning on an air conditioner according to another exemplary embodiment of the present disclosure. Such device for turning on the air conditioner may be used in the wearable device 110, the air conditioner 120, or the relay device 130 as shown in FIG. 1, so as to execute all or part of the steps of the method shown in any one of FIGS. 2 to 4. As shown in FIG. 6, such device for turning on the air conditioner includes, but is not limited to, the sensor parameter acquiring module 501, the physiological parameter determining module 502, the state change determining module 503, the detecting module 504, and the controlling module 505 (FIG. 5).

The physiological parameter is at least one of a heart rate parameter, a body temperature parameter, and a body movement parameter. The physiological parameter determining module 502 includes: a first determining sub-module 502a, a second determining sub-module 502b, and a third determining sub-module 502c.

The first determining sub-module 502a is configured to determine the heart rate parameter based on a parameter collected by an infrared sensor or a piezoelectric sensor in the wearable device.

The second determining sub-module 502b is configured to determine the body temperature parameter based on a parameter collected by a temperature sensor in the wearable device.

The third determining sub-module 502c is configured to determine the body movement parameter based on a parameter collected by a body movement sensor in the wearable device.

The sleep state includes at least a deep sleep state and a light sleep state. The predetermined condition includes a transition from the deep sleep state to the light sleep state.

The device further includes a time period length determining module 506, configured to determine an estimated length of time period $t_1$ during which the user will be in the light sleep state prior to turning on the air conditioner for heating by the controlling module 505.

The controlling module 505 includes a first controlling sub-module 505a and a second controlling sub-module 505b.

The first controlling sub-module 505a is configured to turn on the air conditioner for heating immediately when the change in the sleep state is detected to be in conformity with the predetermined condition in the case of $t_1 \leq t_2$.

The second controlling sub-module 505b is configured to turn on the air conditioner for heating after a time period $(t_1-t_2)$ from the change in the sleep state being detected to be in conformity with the predetermined condition in the case of $t_1 > t_2$.

Here, $t_2$ represents an estimated length of time period during which a room temperature will be heated to a target temperature by the air conditioner.

The time period length determining module 506 includes a state information acquiring sub-module 506a and a time period length determining sub-module 506b.

The state information acquiring sub-module 506a is configured to acquire historical sleep state information including every historical time period during which the user was in the light sleep state.

The time period length determining sub-module 506b is configured to determine an average length of the historical time periods during which the user was in the light sleep state as the estimated length of time period $t_1$.

The device further includes a determining module 507, configured to determine whether a time point of detecting, at which the change in the sleep state is detected to be in conformity with the predetermined condition, is within a predetermined time period before the controlling module 505 turns on the air conditioner for heating. The controlling module 505 is configured to turn on the air conditioner for heating when the time point of detecting is within the predetermined time period.

In summary, the device for turning on the air conditioner according to the embodiments of the present disclosure may determine the change in the sleep state of a user wearing the wearable device on a basis of the physiological parameter, which is determined based on the sensor parameter collected by the wearable device. In the case that the change in the sleep state is in conformity with the predetermined condition, then the air conditioner is turned on for heating when the user wakes up, thereby ensuring that the room temperature has been elevated to an appropriate temperature when the user wakes up. Besides, the user is not required to manually set up the time of turning on the air conditioner. As a result, operations by the users may be simplified, and the users' experience may be improved.

Besides, the device for turning on the air conditioner according to the embodiments of the present disclosure may determine the estimated length of time period during which the user will be in the light sleep state based on the user's historical sleep state information, and determine the specific time of turning on the air conditioner based on the relationship between the estimated length of time period during which the user will be in the light sleep state and the estimated length of time period during which the room temperature will be heated to the target temperature, before the air conditioner is turned on for heating, thereby avoiding unnecessary electric power consumption.

In addition, the device for turning on the air conditioner according to the embodiments of the present disclosure may turn on the air conditioner for heating only if the time point of detecting, at which the change in the sleep state is detected to be in conformity with the predetermined condition, is within the predetermined time period, thereby preventing the air conditioner from being turned on when it should not be turned on.

Figure 7:
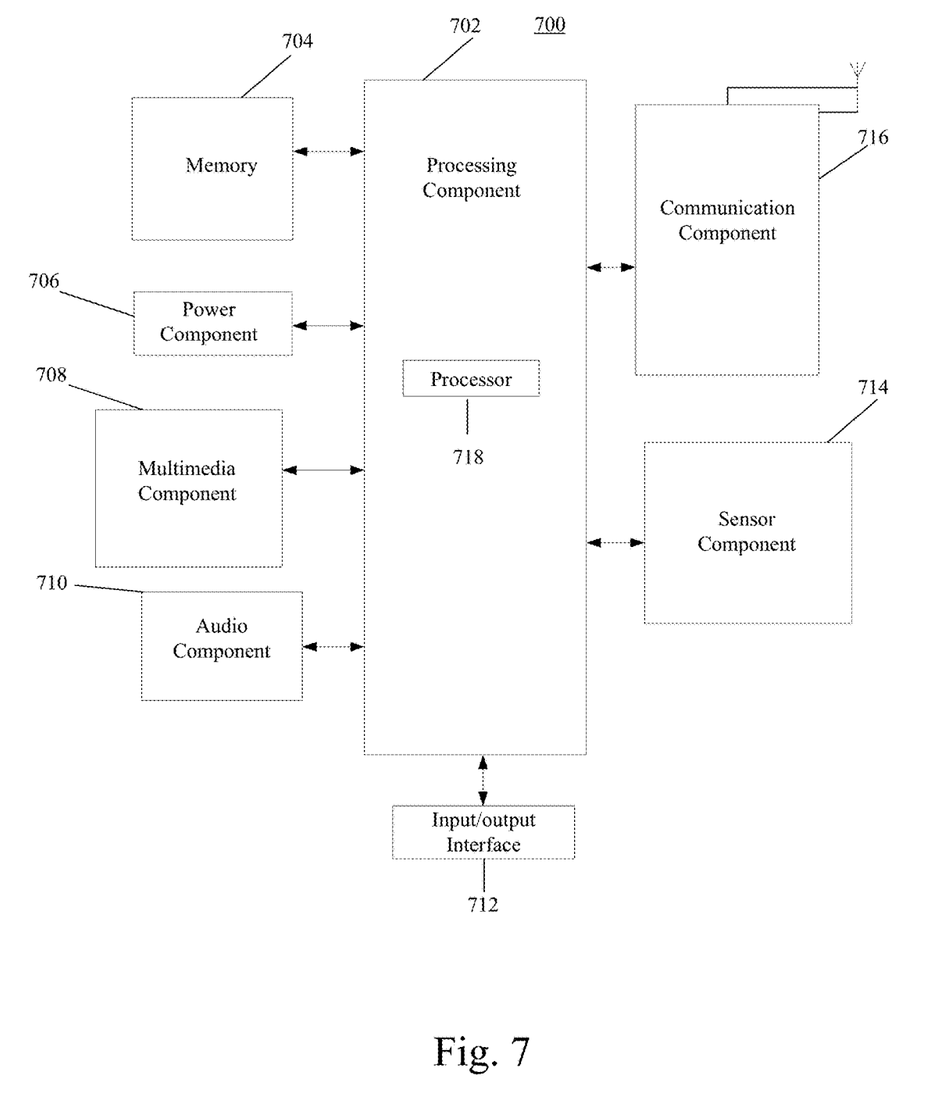
FIG. 7 is a block diagram showing a device for turning on an air conditioner, according to an exemplary embodiment of the present disclosure.

FIG. 7 is a block diagram showing a device 700 according to an exemplary embodiment of the present disclosure. For example, the device 700 may be a mobile phone, a computer, a digital broadcasting terminal, a message sending and receiving device, a router device, a game console, a flat panel device, a medical device, a fitness device, a personal digital assistant, a smart control device, a smart household appliance device, a smart wearable device, or the like.

Referring to FIG. 7, the device 700 may include one or more of the following components: a processing component 702, a memory 704, a power component 706, a multimedia component 708, an audio component 710, an input/output (I/O) interface 712, a sensor component 714, and a communication component 716.

The processing component 702 typically controls overall operations of the device 700, such as the operations associated with display, telephone calls, data communications, camera operations, and recording operations. The processing component 702 may include one or more processors 718 to execute instructions to perform all or part of the steps in the above described methods. Moreover, the processing component 702 may include one or more modules which facilitate the interaction between the processing component 702 and other components. For instance, the processing component 702 may include a multimedia module to facilitate the interaction between the multimedia component 708 and the processing component 702.

The memory 704 is configured to store various types of data to support the operation of the device 700. Examples of such data include instructions for any applications or methods operated on the device 700, contact data, phonebook data, messages, pictures, video, etc. The memory 704 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk. The memory 704 may include one or more modules which are configured to be executed by one or more processors 718, so as to perform all or part of the steps in the above described method shown in any one of FIGS. 2-4.

The power component 706 provides power to various components of the device 700. The power component 706 may include a power management system, one or more power sources, and any other components associated with the generation, management, and distribution of power in the device 700.

The multimedia component 708 includes a screen providing an output interface between the device 700 and the user. In some embodiments, the screen may include a liquid crystal display (LCD) and a touch panel (TP). If the screen includes the touch panel, the screen may be implemented as a touch screen to receive input signals from the user. The touch panel includes one or more touch sensors to sense touches, swipes, and gestures on the touch panel. The touch sensors may not only sense a boundary of a touch or swipe action, but also sense a period of time and a pressure associated with the touch or swipe action. In some embodiments, the multimedia component 708 includes a front camera and/or a rear camera. The front camera and the rear camera may receive an external multimedia datum while the device 700 is in an operation mode, such as a photographing mode or a video mode. Each of the front camera and the rear camera may be a fixed optical lens system or have focus and optical zoom capability.

The audio component 710 is configured to output and/or input audio signals. For example, the audio component 710 includes a microphone configured to receive an external audio signal when the device 700 is in an operation mode, such as a call mode, a recording mode, and a voice recognition mode. The received audio signal may be further stored in the memory 704 or transmitted via the communication component 716. In some embodiments, the audio component 710 further includes a speaker to output audio signals.

The I/O interface 712 provides an interface between the processing component 702 and peripheral interface modules, such as a keyboard, a click wheel, buttons, and the like. The buttons may include, but are not limited to, a home button, a volume button, a starting button, and a locking button.

The sensor component 714 includes one or more sensors to provide status assessments of various aspects of the device 700. For instance, the sensor component 714 may detect an open/closed status of the device 700, relative positioning of components, e.g., the display and the keypad, of the device 700, a change in position of the device 700 or a component of the device 700, a presence or absence of user contact with the device 700, an orientation or an acceleration/deceleration of the device 700, and a change in temperature of the device 700. The sensor component 714 may include a proximity sensor configured to detect the presence of nearby objects without any physical contact. The sensor component 714 may also include a light sensor, such as a CMOS or CCD image sensor, for use in imaging applications. In some embodiments, the sensor component 714 may also include an accelerometer sensor, a gyroscope sensor, a magnetic sensor, a pressure sensor, or a temperature sensor.

The communication component 716 is configured to facilitate communication, wired or wirelessly, between the device 700 and other devices. The device 700 can access a wireless network based on a communication standard, such as WiFi, 2G, or 3G, or a combination thereof. In one exemplary embodiment, the communication component 716 receives a broadcast signal or broadcast associated information from an external broadcast management system via a broadcast channel. In one exemplary embodiment, the communication component 716 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In some exemplary embodiments, the device 700 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In some exemplary embodiments, there is also provided a non-transitory computer-readable storage medium including instructions, such as included in the memory 704, executable by the processor 718 in the device 700, for performing the above-described methods. For example, the non-transitory computer-readable storage medium may be a ROM, a RAM, a CD-ROM, a magnetic tape, a floppy disc, an optical data storage device, and the like.

For the device in the above-mentioned embodiments, the specific manners for performing operations for individual modules therein have been described in detail in method embodiments of the present disclosure, which are not repeated herein.

Although the above described methods and devices turn on the air conditioner for heating in the exemplary embodiments, one of ordinary skill in the art will understand that the present disclosure is not so limited, and the above described methods and devices can also be used to turn on the air conditioner for cooling.

Other embodiments of the invention will be apparent to those skilled in the art from consideration of the specification and practice of the invention disclosed here. This application is intended to cover any variations, uses, or adaptations of the invention following the general principles thereof and including such departures from the present disclosure as come within known or customary practice in the art. It is intended that the specification and examples be considered as example only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A method for turning on an air conditioner, comprising:
   acquiring a sensor parameter collected by a sensor in a wearable device;
   determining a physiological parameter based on the sensor parameter;
   determining a change in a sleep state of a user wearing the wearable device based on the physiological parameter, the sleep state comprising at least a deep sleep state and a light sleep state;
   detecting whether the change in the sleep state is in conformity with a predetermined condition, the predetermined condition comprising a transition from the deep sleep state to the light sleep state; and
   turning on the air conditioner when the change in the sleep state is detected to be in conformity with the predetermined condition,
   wherein prior to turning on the air conditioner, the method further comprises determining an estimated length of time period $t_1$ during which the user will be in the light sleep state, and
   the turning on the air conditioner comprises:
      turning on the air conditioner immediately when the change in the sleep state is detected to be in conformity with the predetermined condition in the case of $t_1 \leq t_2$; and
      turning on the air conditioner after a time period $(t_1-t_2)$ from the change in the sleep state being detected to be in conformity with the predetermined condition in the case of $t_1 > t_2$,
      wherein $t_2$ represents an estimated length of time period during which a room temperature will be adjusted to a target temperature by the air conditioner.

2. The method according to claim 1, wherein the physiological parameter is at least one of a heart rate parameter, a body temperature parameter, or a body movement parameter, and
   the determining a physiological parameter based on the sensor parameter comprises at least one of:
   determining the heart rate parameter based on a parameter collected by an infrared sensor or a piezoelectric sensor in the wearable device;
   determining the body temperature parameter based on a parameter collected by a temperature sensor in the wearable device; or
   determining the body movement parameter based on a parameter collected by a body movement sensor in the wearable device.

3. The method according to claim 1, wherein the determining an estimated length of time period $t_1$ during which the user will be in the light sleep state comprises:
   acquiring historical sleep state information including each historical time period during which the user was in the light sleep state; and
   determining an average length of the historical time periods during which the user was in the light sleep state as the estimated length of time period $t_1$.

4. The method according to claim 1, wherein prior to turning on the air conditioner, the method further comprises:
   determining whether a time point of detecting, at which the change in the sleep state is detected to be in conformity with the predetermined condition, is within a predetermined time period; and
   turning on the air conditioner when the time point of detecting is within the predetermined time period.

5. A device for turning on an air conditioner, comprising:
   a processor; and
   a memory configured to store instructions executable by the processor,
   wherein the processer is configured to:
      acquire a sensor parameter collected by a wearable device;

determine a physiological parameter based on the sensor parameter;

determine a change in a sleep state of a user wearing the wearable device based on the physiological parameter, wherein the sleep state comprises at least a deep sleep state and a light sleep state;

detect whether the change in the sleep state is in conformity with a predetermined condition, wherein the predetermined condition comprises a transition from the deep sleep state to the light sleep state; and turn on the air conditioner when the change in the sleep state is detected to be in conformity with the predetermined condition, wherein the processor is further configured to determine an estimated length of time period $t_1$ during which the user will be in the light sleep state prior to turning on the air conditioner, and the processor is further configured to:

turn on the air conditioner immediately when the change in the sleep state is detected to be in conformity with the predetermined condition in the case of $t_1 \leq t_2$; and turn on the air conditioner after a time period $(t_1-t_2)$ from the change in the sleep state being detected to be in conformity with the predetermined condition in the case of $t_1 > t_2$, wherein $t_2$ represents an estimated length of time period during which a room temperature will be adjusted to a target temperature by the air conditioner.

6. The device according to claim 5, wherein the physiological parameter is at least one of a heart rate parameter, a body temperature parameter, or a body movement parameter, and the processor is configured to determine a physiological parameter based on the sensor parameter by performing at least one of:

determining the heart rate parameter based on a parameter collected by an infrared sensor or a piezoelectric sensor in the wearable device;

determining the body temperature parameter based on a parameter collected by a temperature sensor in the wearable device; or determining the body movement parameter based on a parameter collected by a body movement sensor in the wearable device.

7. The device according to claim 5, wherein the processor is configured to determine an estimated length of time period $t_1$ during which the user will be in the light sleep state time by:

acquiring historical sleep state information including each historical time period during which the user was in the light sleep state; and determining an average length of the historical time periods during which the user was in the light sleep state as the estimated length of time period $t_1$.

8. The device according to claim 5, wherein the processer is further configured to:

determine whether a time point of detecting, at which the change in the sleep state is detected to be in conformity with the predetermined condition, is within a predetermined time period prior to turning on the air conditioner; and turn on the air conditioner when the time point of detecting is within the predetermined time period.

9. A non-transitory computer-readable storage medium having stored therein instructions that, when executed by a processor of a device, cause the device to perform a method for turning on an air conditioner, the method comprising:

acquiring a sensor parameter collected by a sensor in a wearable device;

determining a physiological parameter based on the sensor parameter;

determining a change in a sleep state of a user wearing the wearable device based on the physiological parameter, the sleep state at least comprising a deep sleep state and a light sleep state;

detecting whether the change in the sleep state is in conformity with a predetermined condition, the predetermined condition comprising a transition from the deep sleep state to the light sleep state; and turning on the air conditioner when the change in the sleep state is detected to be in conformity with the predetermined condition, wherein prior to turning on the air conditioner, the method further comprises determining an estimated length of time period $t_1$ during which the user will be in the light sleep state, and the turning on the air conditioner comprises:

turning on the air conditioner immediately when the change in the sleep state is detected to be in conformity with the predetermined condition in the case of $t_1 \leq t_2$; and turning on the air conditioner after a time period $(t_1-t_2)$ from the change in the sleep state being detected to be in conformity with the predetermined condition in the case of $t_1 > t_2$, wherein $t_2$ represents an estimated length of time period during which a room temperature will be adjusted to a target temperature by the air conditioner.

* * * * *